(12) United States Patent
Huang et al.

(10) Patent No.: US 10,088,345 B1
(45) Date of Patent: Oct. 2, 2018

(54) HAZE AND DEFECT DISTRIBUTION AND APERTURE CONFIGURATION IN SURFACE METROLOGY INSPECTORS

(71) Applicant: KLA-Tencor Corporation, Milpitas, CA (US)

(72) Inventors: Chuanyong Huang, Milpitas, CA (US); Raymond Chu, Cupertino, CA (US); Gordana Neskovic, Santa Clara, CA (US); Dieter Wilk, San Jose, CA (US); Christian Wolters, San Jose, CA (US); Tim Mahatdejkul, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 1172 days.

(21) Appl. No.: 13/693,769

(22) Filed: Dec. 4, 2012

(51) Int. Cl.
*G01N 21/88* (2006.01)
*G01N 21/00* (2006.01)
*G01N 21/47* (2006.01)
*G01D 18/00* (2006.01)

(52) U.S. Cl.
CPC .................................. *G01D 18/008* (2013.01)

(58) Field of Classification Search
CPC ............. G01N 21/956; G01N 21/9501; G01N 21/8806; G01N 21/94; G01N 21/47; G03F 1/84; G06T 2207/30148; H01L 22/12

USPC ...................... 356/237.1, 237.2, 237.4, 237.5
See application file for complete search history.

(56) References Cited

U.S. PATENT DOCUMENTS

| | | | | |
|---|---|---|---|---|
| 6,137,570 A | * | 10/2000 | Chuang | G01N 21/9501 250/559.04 |
| 7,554,656 B2 | | 6/2009 | Shortt et al. | |
| 8,908,175 B1 | * | 12/2014 | Kandel | G01N 21/211 356/237.4 |
| 2007/0081154 A1 | * | 4/2007 | Mapoles | G01N 21/47 356/237.5 |
| 2008/0018887 A1 | * | 1/2008 | Chen | G01N 21/47 356/237.2 |
| 2010/0225913 A1 | * | 9/2010 | Trainer | G01N 15/0205 356/338 |
| 2012/0092656 A1 | * | 4/2012 | Nakao | G01N 21/8851 356/237.3 |
| 2015/0212012 A1 | * | 7/2015 | Barak | G02B 21/0016 702/182 |

* cited by examiner

*Primary Examiner* — Roy Y Yi
*Assistant Examiner* — Jeffrey Aiello
(74) *Attorney, Agent, or Firm* — Suiter Swantz pc llo

(57) ABSTRACT

The present disclosure is directed to a method for designing an aperture in a mask for inspecting a wafer. The method includes the steps of scanning a collection plane of the wafer at a plurality of points and collecting data for at least a part of the wafer. The method also includes the step of mapping the data. A further step of the method includes configuring the aperture based on the mapped data.

16 Claims, 11 Drawing Sheets

HAZE AND DEFECT DISTRIBUTION AND APERTURE CONFIGURATION IN SURFACE METROLOGY INSPECTORS

TECHNICAL FIELD

The disclosure generally relates to the field of wafer inspection, and more particularly to a system and method for measuring haze and defect distribution of a wafer.

BACKGROUND

Current systems and methods for measuring the haze spatial distribution of a semiconductor wafer may involve the use of an atomic force microscope. An atomic force microscope may be used to measure surface roughness of a micro area of the wafer, calculate the power spectral density, and then use the measurements for the micro area to extrapolate the roughness of the entire surface area of the wafer using computer aided calculations.

Another method for measuring the haze distribution of a semiconductor wafer may involve a surface scatter inspection system and measuring the light scattering intensity at specific areas of the wafer.

There also exist methods for determining scattering signal of defects on the surface of a wafer. For example, one existing method involves using the refractive index and absorption coefficient in computer-aided simulation. The optical aperture of the inspection tool may be designed based on a simulation of the defects and a calculation of the signal-to-noise ratio.

The existing methods for measuring haze and defect signal spatial distribution may present a variety of inadequacies. For example, atomic force microscope measurements may be slow and provide detection that is so localized that it is not truly representative of the wafer as a whole. In addition, atomic force microscope measurements may not provide direct light scattering property of a wafer.

The existing methods for measuring haze spatial distribution may also involve determining haze spatial distribution by extrapolating the measurements from a portion of the wafer to the remaining surface area of the wafer. Using a limited area to extrapolate the haze spatial distribution may not provide the level of accuracy needed to meet performance requirements of scatter based inspection systems. In addition, manual methods of measuring haze spatial distribution may not be repeatable.

The many shortcomings of current techniques give rise to a need for a repeatable method and apparatus for measuring haze spatial distribution as well as the defect scattering to haze scattering spatial distribution ratio of a wafer.

SUMMARY

The present disclosure is directed to a method for visualizing haze and defect signal spatial distribution of a wafer, as well as a method for designing an aperture for inspecting a wafer. The method may include the step of inspecting the surface of the wafer and collecting data at a plurality of rotating pin-hole positions on the scattering collection plane. The method also includes the steps of analyzing and mapping the data. A further step of the method includes designing the aperture based on the mapped data. This method may improve the design of the aperture and sensitivity of an inspection system.

The present disclosure is also directed to a system for visualizing haze and defect signal distribution of a wafer.

Using the system, an aperture in a mask may be reconfigured in real time. The system may include a collector configured for collecting scattering data of the wafer. The system may also include mask, which is configured to include an aperture. The system also includes a control module configured for controlling the movements of the mask. A processor configured for analyzing and mapping the scattering distribution of haze and defects is also included in the system.

The present disclosure is also directed to a method for designing an aperture in a mask for inspecting a wafer. The method includes the steps of scanning a collection plane of the wafer at a plurality of points and collecting data for at least a part of the wafer. The method also includes the step of mapping the data. A further step of the method includes configuring the aperture based on the mapped data.

The present disclosure is also directed to a method for visualizing a haze and a defect signal distribution of a wafer. The method includes the step of collecting data for the wafer. This data is then used to plot a haze distribution of the wafer in a further step of the method. The method also includes the step of receiving an election of at least one defect of interest. A further step of the method includes mapping at least one defect of interest. The method also includes the step of mapping a signal-to-noise ratio distribution of the at least one defect of interest. The method also includes the step of configuring an aperture in a mask for inspecting the wafer such that the aperture is open where the signal-to-noise ratio is above a predetermined threshold and the aperture is closed when the signal-to-noise ratio distribution is below a predetermined threshold. A further step of the method includes inspecting the wafer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure is directed to a method for visualizing haze and defect signal spatial distribution of a wafer, as well as a method for designing an aperture for inspecting a wafer. The method may include the step of inspecting the surface of the wafer and collecting data at a plurality of rotating pin-hole positions on the scattering collection plane. The method also includes the steps of analyzing and mapping the data. A further step of the method includes designing the aperture based on the mapped data. This method may improve the design of the aperture and sensitivity of an inspection system.

Figure 1:
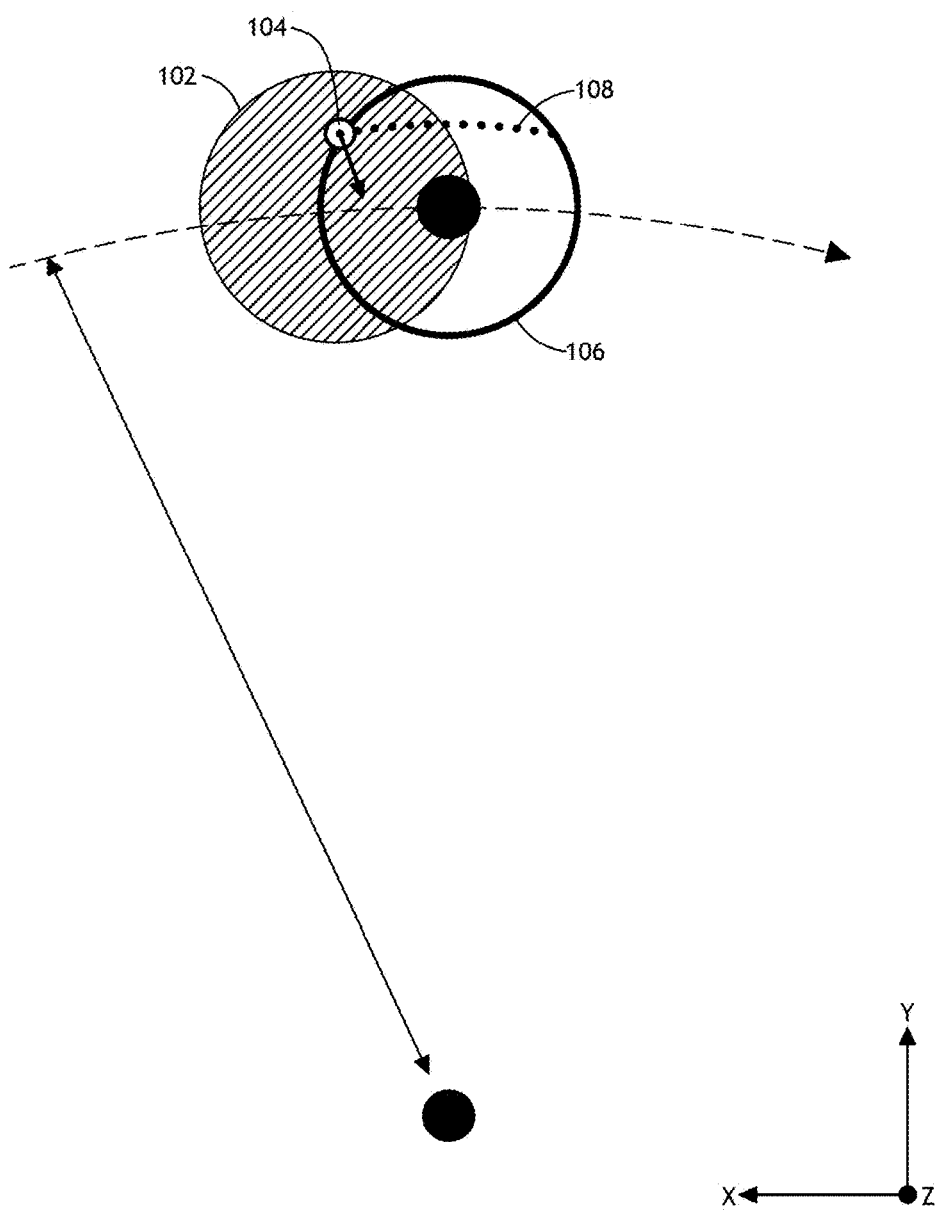
FIG. 1 shows the movement of a rotating pin-hole hardware scanning through the scattering collection plane in accordance with the systems and methods of the present disclosure.

FIG. 1 shows the movement of the rotating pin-hole hardware through the scattering collection plane. Data may be collected, while inspecting the wafer at a plurality of points 108, through the pin-hole hardware or mask 102. This may be performed by a collector or a series of collectors. This step may include using a mask 102 with an aperture 104 to scan the scattering collection plane at a plurality of data points 108. The mask 102 may be positioned over a collector plane 106. The mask 102 may be programmed to rotate automatically and change its position at each inspection scan of a wafer so that the aperture 104 is positioned over a plurality of locations on the collector plane. Therefore, at each position of mask 102, a wafer scan map of defects and the associated background haze are obtained. The mask 102 may be integrated into the inspection tool and this scanning feature becomes part of a system inspection optimization or improvement function. In one embodiment, the mask 102 with the aperture 104 is a blind aperture, meaning the mask 102 includes just one aperture 104. In alternative embodiments, the mask 102 may include additional apertures 104 that may have different shapes, sizes, and locations. Similarly, in alternative embodiments the inspecting of the wafer may include swathing and linear scanning to sample the wafer.

The step of collecting data of a wafer may include collecting scattering signal of air, haze, natural defects, Polystyrene Latex or other deposited defects and obtaining distribution data of defect-defect ratio and signal-haze ratios of the aforementioned. The data may be collected through several collectors, detectors, and other instruments.

In one embodiment, haze data is represented as the average haze of the entire inspection area of a wafer. In this embodiment, defects at each data collection point are registered by their location along an x axis and a y axis location on the wafer. Accordingly, defects at a particular x, y location on the wafer can be analyzed at each of the collection points of the scattering collection plane. A scattering distribution map for each defect or defects is obtained.

In another embodiment, haze data can be taken at the location of the defect or defects. This allows a localized haze and defect scattering distribution to be obtained.

Figure 2:
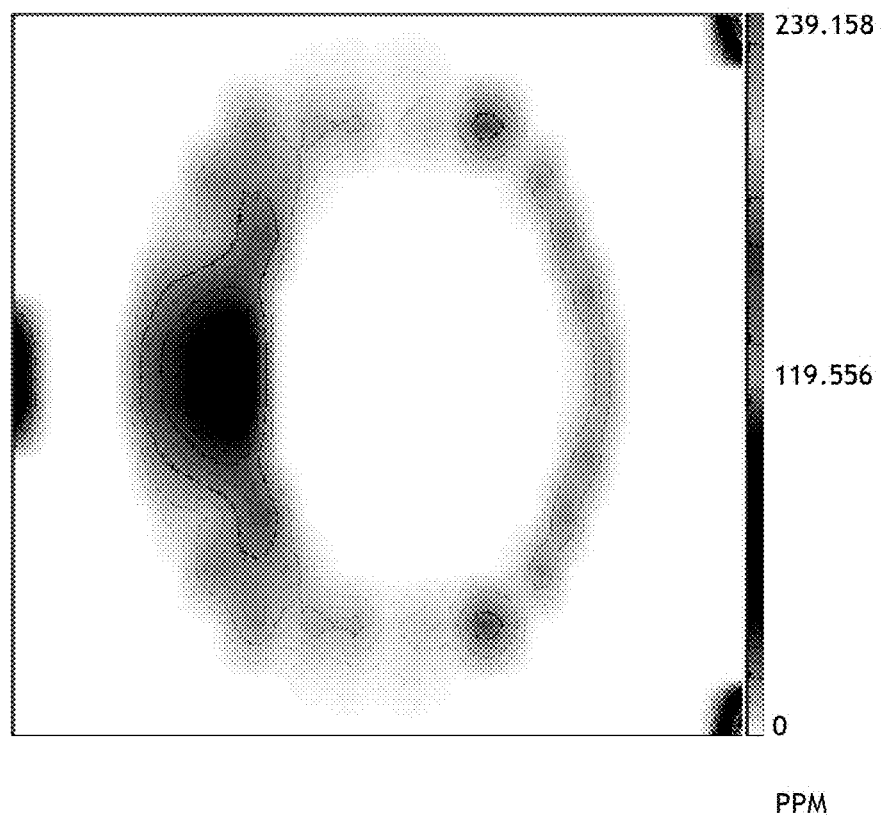
FIG. 2 is an example of haze spatial distribution data for an example wafer.

The method also includes the step of mapping the collected data. The collected data may be analyzed and mapped using software in one embodiment. An example of mapped haze data for a tungsten semiconductor wafer is provided in FIG. 2. In the example, haze data has been collected for the wafer and a haze map has been generated as the average haze of the wafer at each collection position 108 in parts per million (PPM). Furthermore, defects scattering data is collected and may be used to generate a particle defect map as shown in the example in FIG. 3. In the particle defect map shown in FIG. 3, the particle defects are measured in units of Micron Latex Sphere Equivalents (umLSE). Specifically, the particle defect map shows the diameter of the defects in microns of the Polystyrene Latex Sphere having a scattering intensity equal to the scattering intensity of the defect.

It may also be possible to prepare additional mapping of the particle defects identified on the wafer. For example, a defect of interest may be identified from the particle defect map in FIG. 3, and additional mapping for the defect may be performed. For example, FIG. 4 shows a Polystyrene Latex/haze plot for a cluster of Polystyrene Latex defects identified in the particle defect map provided in FIG. 3.

Figure 3:
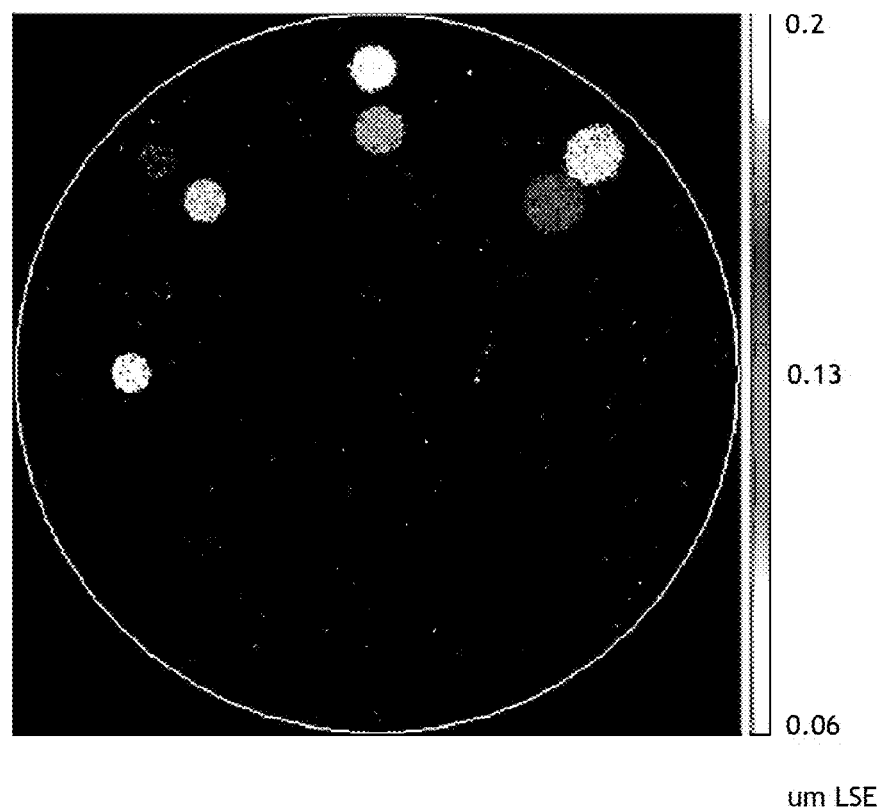
FIG. 3 is an example of a wafer deposited with clustered defects of specific sizes.
Figure 4:
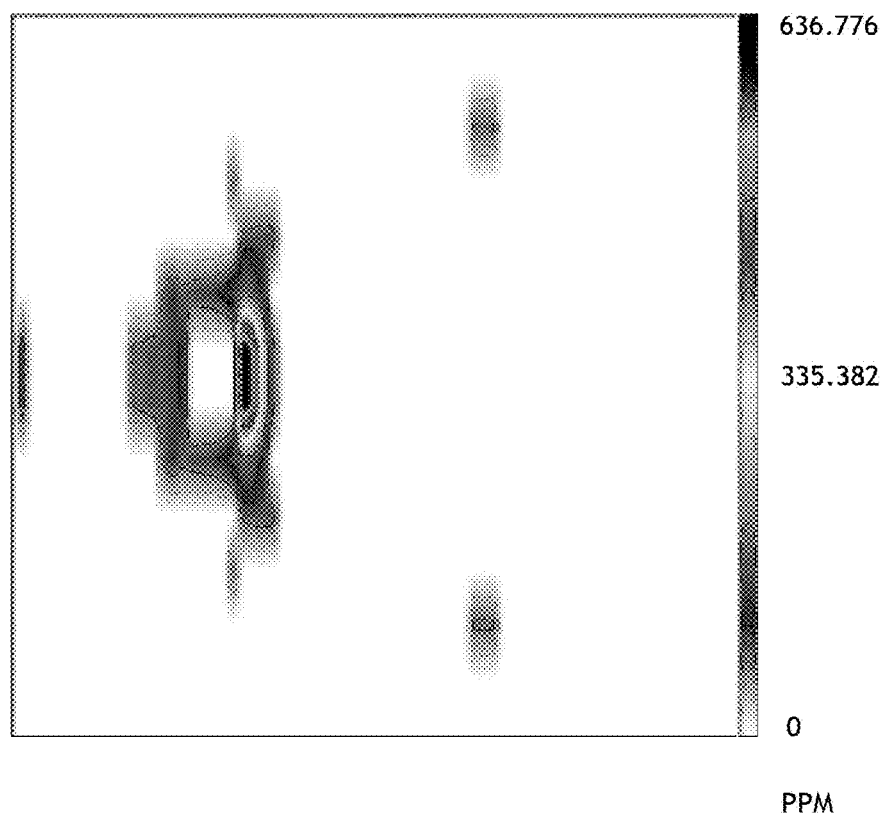
FIG. 4 shows a defect scattering spatial distribution of one of the clustered defects in the wafer shown in FIG. 3.
Figure 5:
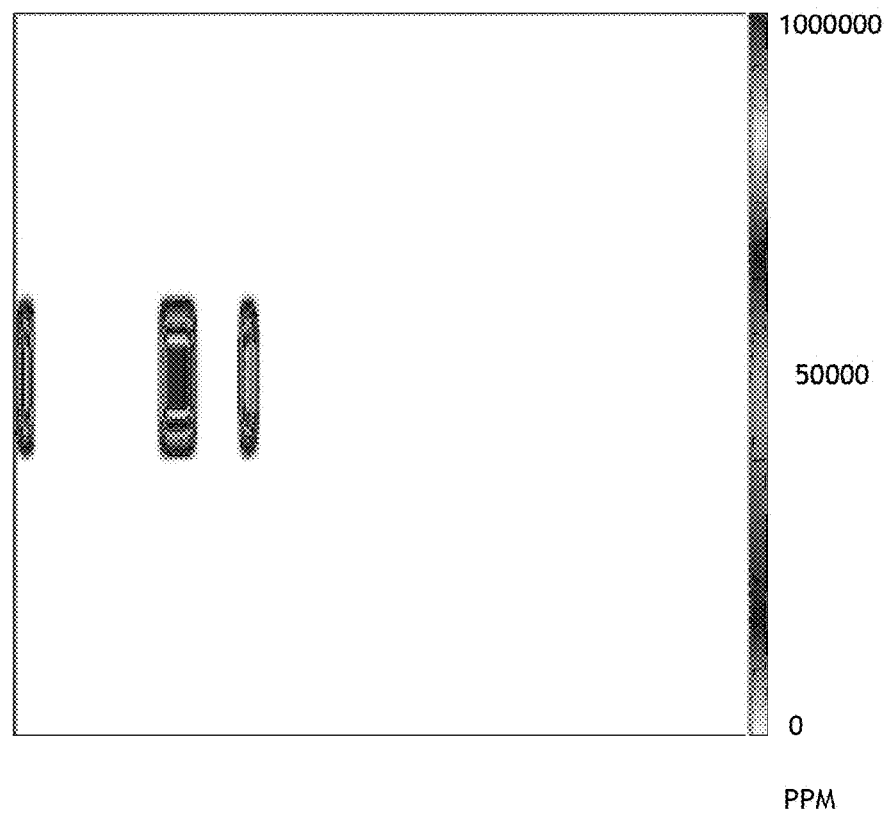
FIG. 5 shows a defect scattering spatial distribution for a collection of natural defects of the wafer.

Based on the random locations of the natural defects the defect/haze map may be generated for the natural defects and natural defects may be identified from the particle defect map shown in FIG. 3. FIG. 5 shows a scattering distribution on the collection plane for a collection of natural defects identified by their locations on the wafer in the particle defect map provided in FIG. 3.

Figure 6:
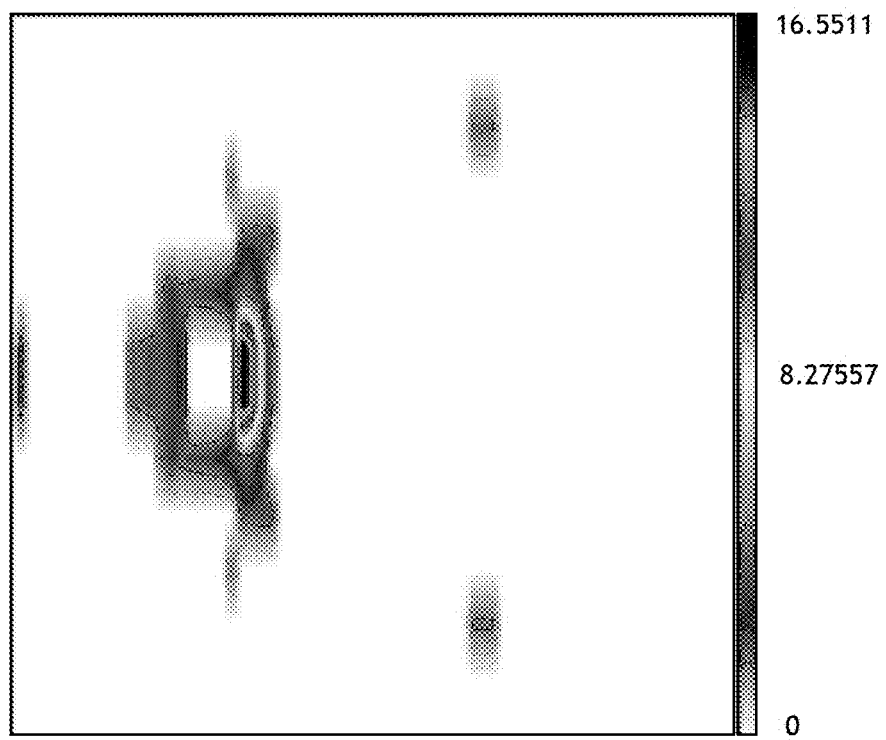
FIG. 6 is an example of signal-to-noise ratio spatial distribution of one of the clustered defects of the example wafer.

An additional step of the method may involve generating a signal-to-noise ratio distribution based on the collected data. An example signal-to-noise ratio distribution for the example wafer is provided in FIG. 6. The step of generating a signal-to-noise ratio distribution may be performed using software and algorithms known in the art.

Figure 7:
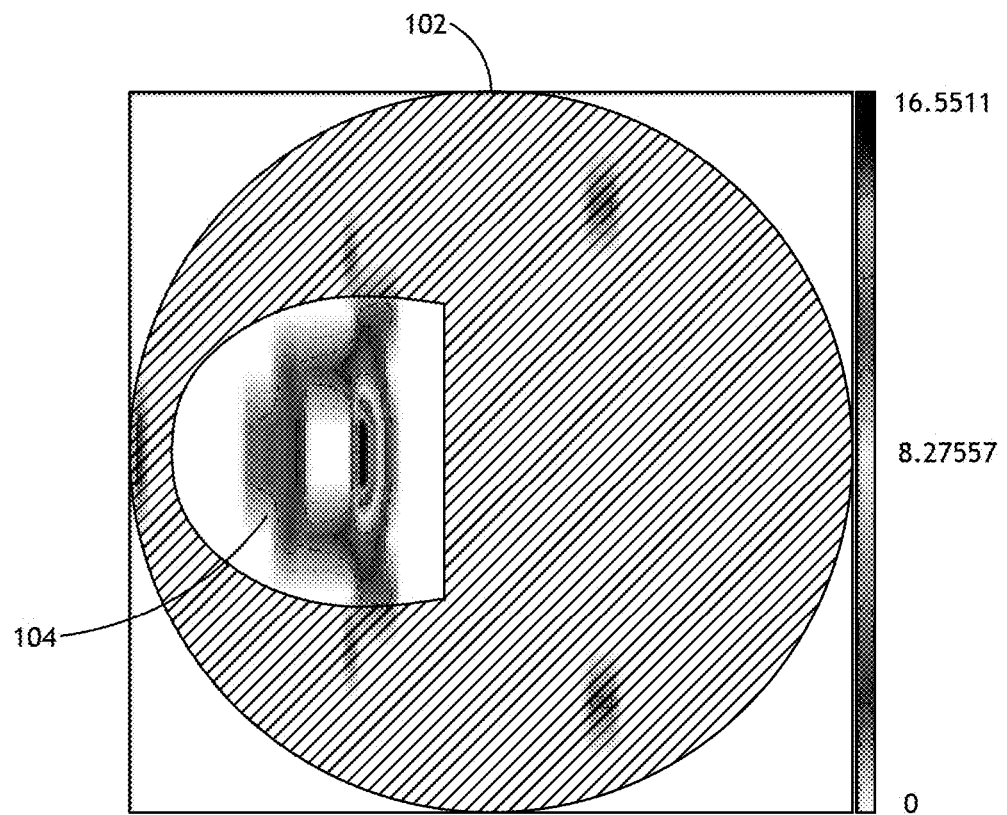
FIG. 7 is an example of an aperture design based on the signal-to-noise ratio distribution from FIG. 6.

The method also includes the step of configuring the aperture based on the mapped signal-to-noise data. For example, the aperture may be configured based on a signal-to-noise ratio distribution that is generated based on the collected data. An example of an aperture configured based on the signal-to-noise ratio distribution is provided in FIG. 7. The mask 102 has been configured to include the aperture 104 in an optimized location based on the signal-to-noise ratio distribution map. The step of configuring the aperture 104 based on the signal-to-noise ratio distribution map may include configuring an aperture 104 that is transparent to a defect signal, if the signal noise ratio at the particular location of the signal-to-noise ratio map is larger than a predetermined threshold. This means configuring an aperture that is open over areas of the mapped data where the signal noise ratio is above a predetermined threshold, and the aperture is closed over areas of the mapped data where the signal-to-noise ratio is below the predetermined threshold.

The method and system of the current disclosure may be useful in any inspection system intended to detect wafer information such as haze and defect scattering spatial distribution. For example, the method may be used in ellipsoidal collection, refractive lens collections, imaging collection systems, multiple collector systems, dark field and bright field collection systems, etc. The method may be useful for configuring the aperture to improve the signal-to-noise ratio and detection sensitivity.

Figure 8:
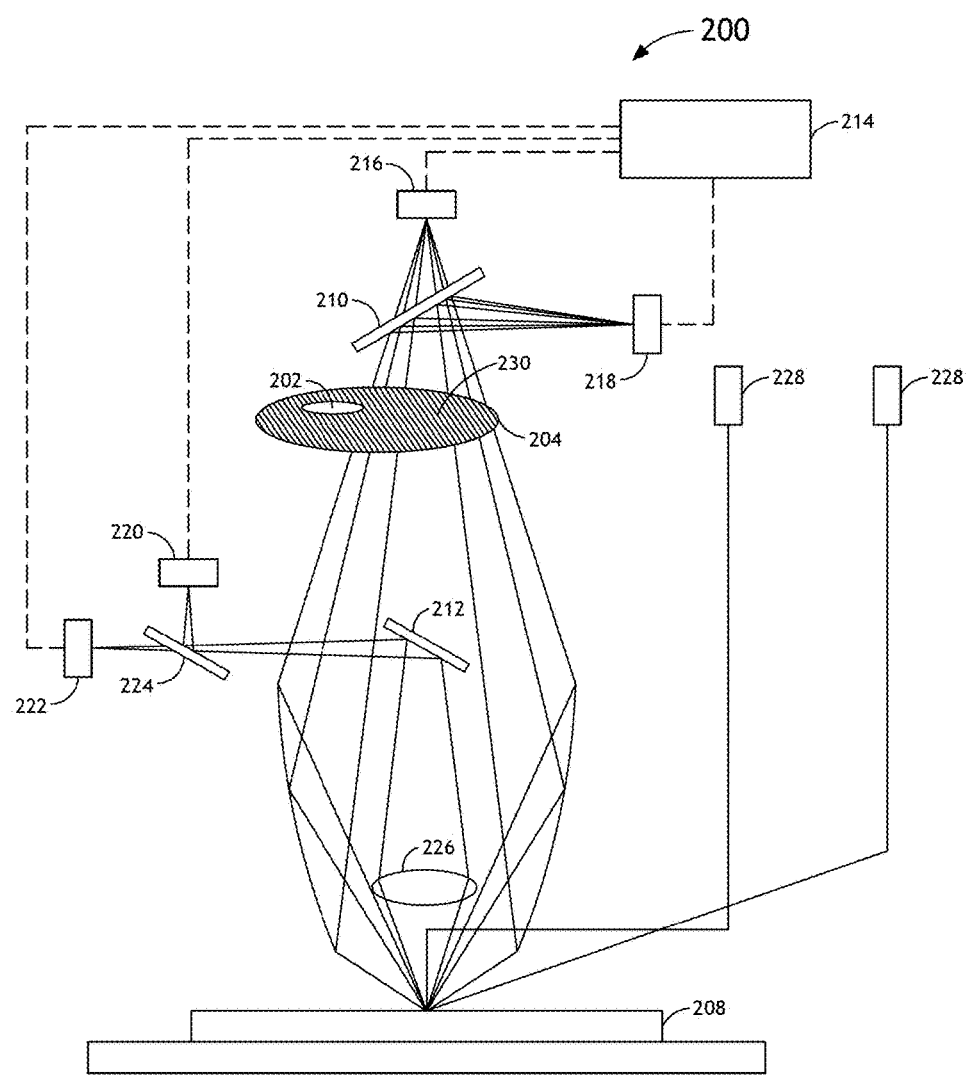
FIG. 8 is an example of an inspection system suitable for implementing the methods in accordance with the present disclosure.

One example of an inspection system 200 suitable for implementing the method in accordance with the present disclosure is provided in FIG. 8. The inspection system 200 may be used to inspect a wafer 208. In one embodiment, the mask 204 with the designed aperture 202 is located between a wide detector 216 and a mirror 212 of the system 200. The system 200 may include additional elements, such as a central processing unit 214, a first wide detector 216, a second wide detector 218, a first narrow detector 220 and a second narrow detector 222, a polarizing beam splitter 224, a lens collector 226, and light sources 228.

In one embodiment, the mask 204 with the designed aperture 202 is located between a wide detector 216 and a mirror 212 of the system 200. However, it may also be possible to locate the mask 204 with the designed aperture 202 in other locations within the system 200. Similarly, the mask 204 with the designed aperture 202 may be combined with other elements. For example, the mask 204 with the designed aperture 202 may be combined with a linear polarizing filter or other polarizing optics or a combination of polarizing elements.

In the example shown in FIG. 8, the closed area 230 of the mask 204 is configured to be non-transparent to the signal, whereas the open area of the aperture 202 in the mask 204 is configured to be transparent to the signal.

Figure 9:
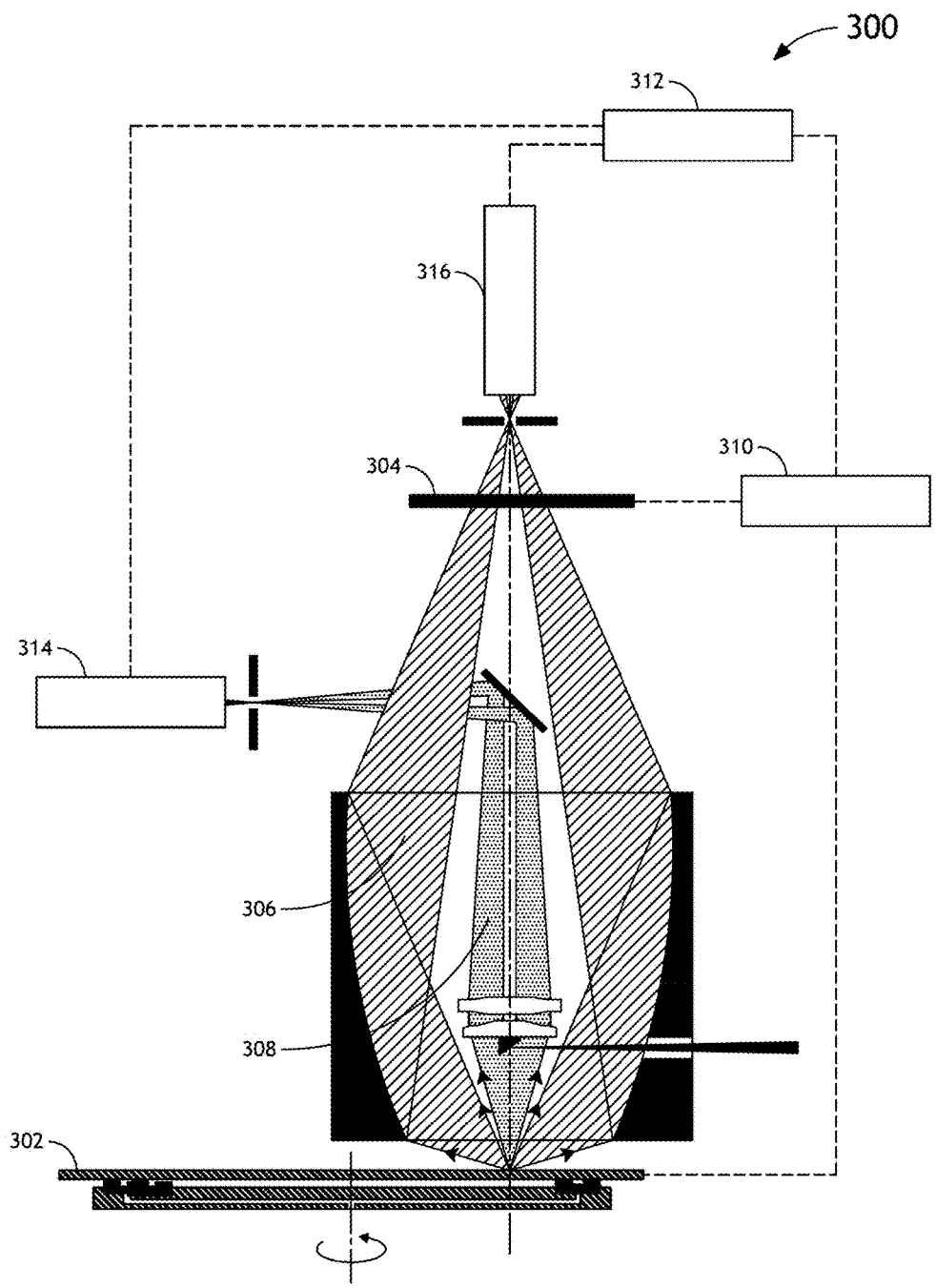
FIG. 9 shows a system for visualizing a haze and a defect signal spatial distribution of a wafer.

The present disclosure is also directed to a system 300 for visualizing haze and defect signal distribution of a wafer 302 as shown in FIG. 9. Using the system 300, the aperture in the mask 304 may be reconfigured in real time. The system 300 may include a collector configured for collecting scattering data of the wafer 302. For example, the collector may include a wide collector 306 and a narrow collector 308. The system 300 may also include mask 304 which is configured to include an aperture. The system 300 also includes a control module 310 configured for controlling the movements of the mask 304. A processor 312 configured for analyzing and mapping the scattering distribution of haze and defects is also included in the system 300. The system 300 may also include additional detectors in one embodiment. For example, the system 300 may also include a narrow detector 314 and a wide detector 316.

The collectors of the system 300 shown in FIG. 9 may be configured to collect scattering data for a part or whole wafer. The scattering data may include air, haze, natural defects data as well as deposited defects data such as Polystyrene Latex defect data and signal-to-noise ratio distribution data for the wafer 302.

The processor 312 of the system 300 shown in FIG. 9 may be configured to map and analyze the collected data for a part of, or the whole wafer 302. The map may include mapping a haze distribution, a defect signal scattering distribution, a signal-to-noise ratio distribution, or a natural defect scattering distribution for the wafer 302.

The system 300 may also include a mask 304. The mask 304 is configured to include an aperture. The aperture is configured based on mapped data for the wafer 302. For example, the aperture of the mask 304 may be configured based on a signal-to-noise ratio distribution of the wafer 302 such that, the aperture is open over areas of the signal-to-noise ratio distribution where the signal-to-noise ratio is above a predetermined threshold and the aperture is closed where the signal-to-noise ratio is below a predetermined threshold.

Figure 10:
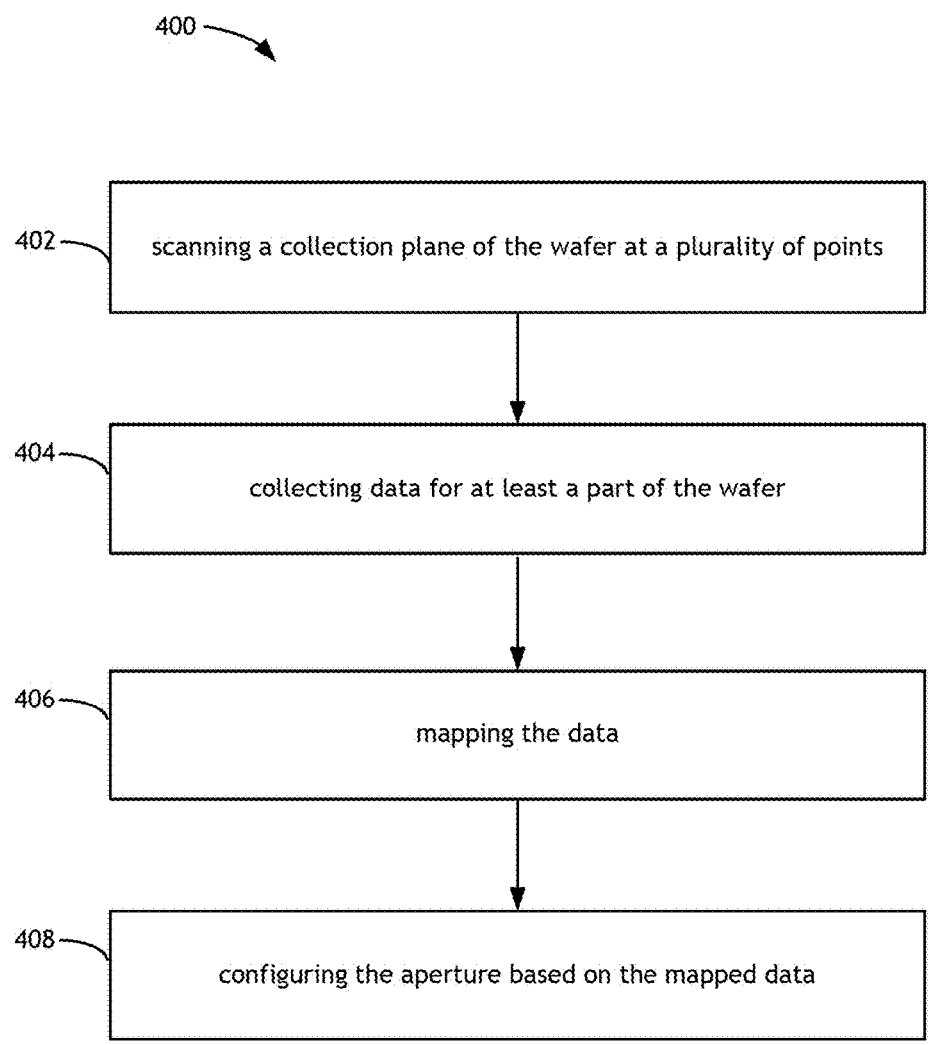
FIG. 10 is a flow diagram of a method for designing an aperture for a wafer.

The present disclosure is also directed to a method 400 for designing an aperture in a mask for inspecting a wafer as shown in the flow diagram provided in FIG. 10. The method includes the steps of scanning a collection plane of the wafer at a plurality of points 402 and collecting data for at least a part of the wafer 404. The method also includes the step of mapping the data 406. A further step of the method includes configuring the aperture based on the mapped data 408.

The step of collecting data for at least a part of the wafer 404 of the method 400 shown in FIG. 10 may include collecting air data, haze data, natural defects data, deposited defects data, and signal-to-noise ratio distribution data for the wafer. The data may be collected for only a portion of the wafer, or may be collected for the entire wafer.

The step of mapping the data 406 may include mapping a haze distribution, a signal defect distribution, a signal-to-noise ratio distribution, or a natural defect distribution for the wafer. The map may cover only a portion of the wafer or the entire wafer.

The step of configuring the aperture based on the mapped data 408 of the method 400 may include configuring an aperture that is open over areas of the mapped data where a signal-to-noise ratio is above a predetermined threshold and the aperture is closed over areas of the mapped data where the signal-to-noise ratio is below a predetermined threshold.

The method 400 shown in FIG. 10 may be performed on a patterned wafer or on an unpatterned wafer. Similarly, the method 400 may be performed on other objects.

The method 400 shown in FIG. 10 may also include the step of receiving an election of a particular particle of interest. For example, a user may review the mapped data for the wafer, such as a particle defect map. Based on the particle defect map, the user may identify a defect of interest, and additional mapping for the defect may be performed. For example, a Polystyrene Latex/haze plot may be prepared for a cluster of Polystyrene Latex defects identified in the particle defect map.

Figure 11:
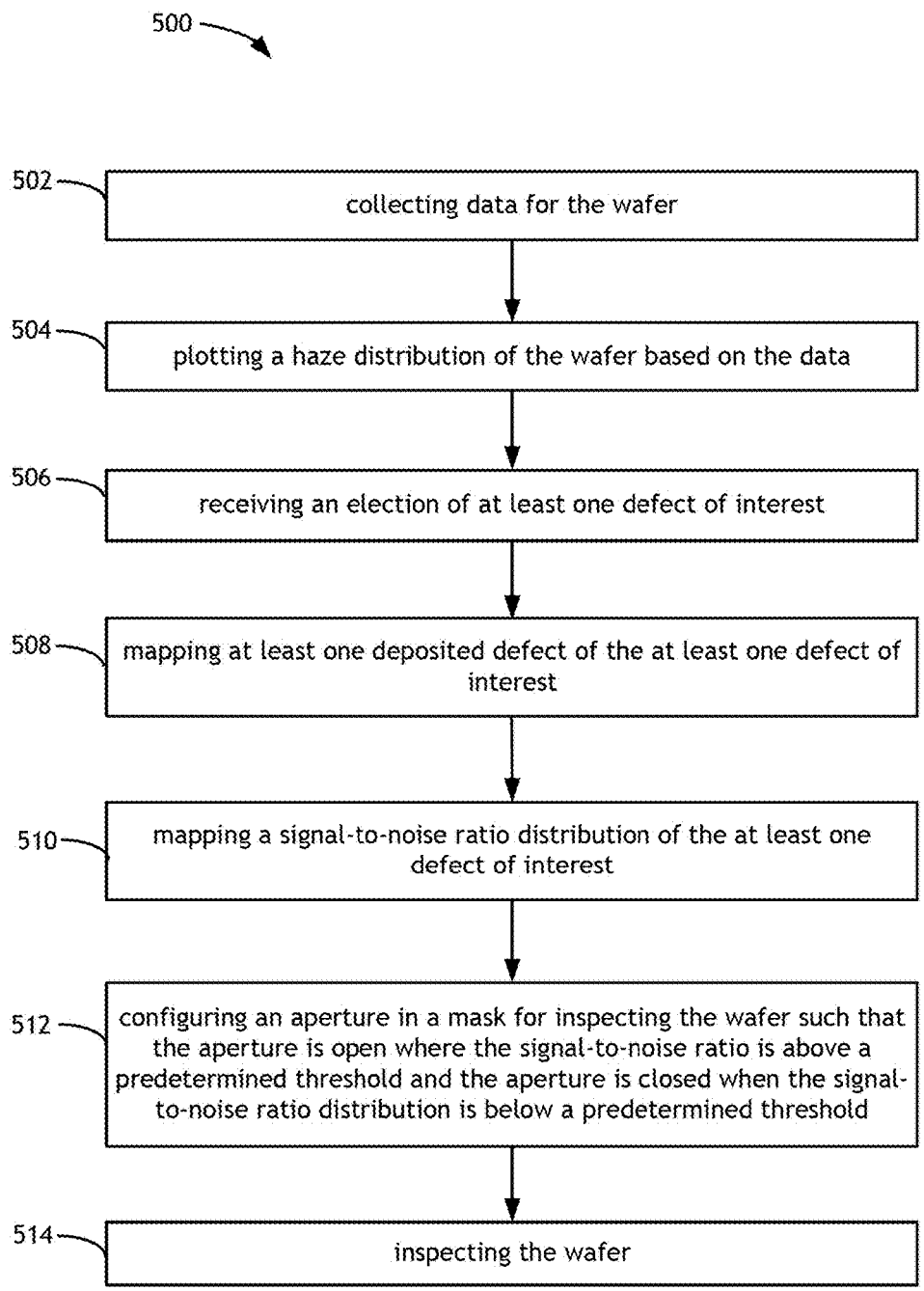
FIG. 11 is a flow diagram of a method for visualizing an aperture for a wafer.

The present disclosure is also directed to a method 500 for visualizing a haze and a defect signal distribution of a wafer. A flow chart depicting the steps of the method 500 is provided in FIG. 11. The method 500 includes the step of collecting data for the wafer 502. This data is then used to plot a haze distribution of the wafer 504 in a further step of the method 500.

The method 500 also includes the step of receiving an election of at least one defect of interest 506. A further step of the method includes mapping at least one defect of interest 508. The method 500 also includes the step of mapping a signal-to-noise ratio distribution of the at least one defect of interest 510. The method 500 also includes the step of configuring an aperture in a mask for inspecting the wafer such that the aperture is open where the signal-to-noise ratio is above a predetermined threshold and the aperture is closed when the signal-to-noise ratio distribution is below a predetermined threshold 512. A further step of the method 500 includes inspecting the wafer 514. The method 500 may be performed continuously or repeatedly in one embodiment.

The systems and methods of the present disclosure may provide a number of advantages. For example, the systems and methods provide automatic measurement of haze and defect signals, as well as optimized optical aperture design based on the measurements. The systems and methods of the present disclosure may also provide improved raw data collection during the wafer inspection process and a flexible scanning range on the whole wafer surface or areas of interest on the wafer. The systems and methods of the present disclosure may also provide simultaneous data collection for visualizing haze, defect, and signal-to-noise ratio data. The systems and methods of the present disclosure may also be automated. Last, the systems and methods of the present disclosure may be integrated into inspection systems for reconfigurable aperture application.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

All of the methods described herein may include storing results of one or more steps of the method embodiments in a storage medium. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

It is further contemplated that each of the embodiments of the method described above may include any other step(s) of any other method(s) described herein. In addition, each of the embodiments of the method described above may be performed by any of the systems described herein.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed is:

1. A method comprising:
   scanning, with a mask including an aperture, a collection plane of a wafer at a plurality of points;
   collecting scattered light passing through the aperture from at least a portion of the wafer at the plurality of points;
   converting the collected light to a collected data signal with one or more detectors;
   determining a scattering distribution within the collected data signal for at least a portion of the wafer with one or more processors;
   adjusting, with a control module, a position of the mask based on the collected data signal such that the mask is open where the signal-to-noise ratio of a defect signal is above a predetermined threshold and the mask is closed where the signal-to-noise ratio of the defect signal is below the predetermined threshold.

2. The method of claim 1, wherein the collected data signal for at least a part of the wafer includes at least one of: air scattering data, haze data, natural defects data, deposited defects data, and signal-to-noise ratio distribution data.

3. The method of claim 1, wherein the determining a scattering distribution within the collected data signal for at least a portion of the wafer includes mapping at least one of: a haze distribution, a signal defect distribution, a signal-to-noise ratio distribution, and a natural defect distribution.

4. The method of claim 1, wherein the wafer includes a patterned wafer.

5. The method of claim 1, wherein the wafer includes an unpatterned wafer.

6. The method of claim 1, further comprising:
   receiving an election of a particular particle of interest.

7. A method comprising:
   scanning, with a mask including an aperture, a collection plane of a wafer at a plurality of points;
   collecting scattered light passing through the aperture from at least a portion of the wafer at the plurality of points;
   converting the collected light to a collected data signal with one or more detectors;
   determining a scattering distribution within the collected data signal for at least a portion of the wafer with one or more processors;
   adjusting, with a control module, a position of the mask based on the collected data signal such that the mask is open where the signal-to-noise ratio of a defect signal is above a predetermined threshold and the mask is closed where the signal-to-noise ratio of the defect signal is below the predetermined threshold; and
   inspecting, with an inspection tool, the wafer.

8. The method of claim 7, wherein the collected data signal for at least a part of the wafer includes at least one of: air scattering data, haze data, natural defects data, deposited defects data, and signal-to-noise ratio distribution data.

9. The method of claim 7, wherein the wafer includes a patterned wafer.

10. The method of claim 7, wherein the wafer includes an unpatterned wafer.

11. A system comprising:
    a mask, the mask including an aperture;
    a control module configured to scan the aperture of the mask across a collection plane of a wafer to collect scattered light passing through the aperture at a plurality of points;
    one or more collectors configured for collecting scattered light from at least a portion of the wafer;
    one or more detectors arranged to receive light collected by the one or more collectors and convert the collected light to a collected data signal;
    a processor, the processor configured for determining a scattering distribution within the collected data signal for at least a part of the wafer; and
    wherein the control module is configured to adjust a position of the mask based on the collected data signal such that the mask is open where the signal-to-noise ratio of a defect signal is above a predetermined threshold and the mask is closed where the signal-to-noise ratio of the defect signal is below the predetermined threshold.

12. The system of claim 11, wherein the collected data signal for at least a part of the wafer includes at least one of: air scattering data, haze data, defect signal data, natural defects data, deposited defects data, and signal-to-noise ratio distribution data.

13. The system of claim 11, wherein the determining a scattering distribution within the collected data signal for at least a part of the wafer includes mapping at least one of: a haze distribution, a defect signal distribution, a signal-to-noise ratio distribution, and a natural defect distribution.

14. The system of claim 11, wherein the wafer includes a patterned wafer.

15. The system of claim 11, wherein the wafer includes an unpatterned wafer.

16. The system of claim 11, wherein the system is at least one of: an ellipsoidal collection system, a refractive lens collection system, an imaging collection system, a multiple collector system, or a dark field and bright field collection system.

* * * * *